(12) United States Patent
Hatta

(10) Patent No.: US 10,375,806 B2
(45) Date of Patent: Aug. 6, 2019

(54) LIGHTING CONTROL SYSTEM, LIGHTING SYSTEM, AND LIGHTING CONTROL METHOD

(71) Applicant: Panasonic Intellectual Property Management Co., Ltd., Osaka (JP)

(72) Inventor: Kazuhiro Hatta, Osaka (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 0 days.

(21) Appl. No.: 16/053,020

(22) Filed: Aug. 2, 2018

(65) Prior Publication Data
US 2019/0053360 A1  Feb. 14, 2019

(30) Foreign Application Priority Data

Aug. 10, 2017 (JP) ................. 2017-154852

(51) Int. Cl.
*H05B 37/02* (2006.01)
*A61M 21/02* (2006.01)
(Continued)

(52) U.S. Cl.
CPC ......... *H05B 37/0281* (2013.01); *A61M 21/02* (2013.01); *A61N 5/0618* (2013.01);
(Continued)

(58) Field of Classification Search
CPC . A61M 21/02; A61N 5/0618; H05B 37/0281; H05B 37/0245
See application file for complete search history.

(56) References Cited

U.S. PATENT DOCUMENTS

| 2010/0063641 | A1* | 3/2010 | Scholten | ............... | G05B 15/02 |
| | | | | | 700/287 |
| 2012/0235579 | A1* | 9/2012 | Chemel | .................. | F21S 2/005 |
| | | | | | 315/152 |

(Continued)

FOREIGN PATENT DOCUMENTS

| JP | H10-321378 A | 12/1998 |
| JP | 2006-344555 A | 12/2006 |

(Continued)

*Primary Examiner* — Douglas W Owens
*Assistant Examiner* — Syed M Kaiser
(74) *Attorney, Agent, or Firm* — McDermott Will & Emery LLP

(57) ABSTRACT

A lighting control system controls a light source that emits light to a space in which subjects stay. The lighting control system includes: an communication interface that obtains stay schedule information indicating scheduled periods in an operation period after a first time and before a second time later than the first time, the scheduled periods being periods during each of which a corresponding one of the subjects is to stay in the space; and a processor that creates an illumination schedule for causing the light source to emit the light, based on the stay schedule information, and causes the light source to emit the light according to the illumination schedule created. The processor creates, based on the stay schedule information, the illumination schedule for causing the light source to emit the light during a period including a scheduled period common to at least two of the subjects.

13 Claims, 12 Drawing Sheets

(51) Int. Cl.
*A61N 5/06* (2006.01)
*A61M 21/00* (2006.01)
(52) U.S. Cl.
CPC ............... *A61M 2021/0044* (2013.01); *A61N 2005/0626* (2013.01)

(56) References Cited

U.S. PATENT DOCUMENTS

| | | | | |
|---|---|---|---|---|
| 2014/0081659 | A1* | 3/2014 | Nawana | G16H 50/20 |
| | | | | 705/3 |
| 2015/0262114 | A1* | 9/2015 | Ming | G06Q 10/063114 |
| | | | | 705/7.15 |
| 2016/0192108 | A1* | 6/2016 | Chaudhary | G06F 8/61 |
| | | | | 455/411 |
| 2017/0208673 | A1* | 7/2017 | Schlangen | H05B 37/0218 |
| 2017/0364648 | A1* | 12/2017 | Leuschner | G06F 19/3481 |
| 2018/0075218 | A1* | 3/2018 | Benefield | G06F 19/324 |
| 2018/0116415 | A1* | 5/2018 | Karschnik | A61M 21/02 |

FOREIGN PATENT DOCUMENTS

| | | | |
|---|---|---|---|
| JP | 2013-246890 A | 12/2013 | |
| JP | 2017-010852 A | 1/2017 | |

\* cited by examiner

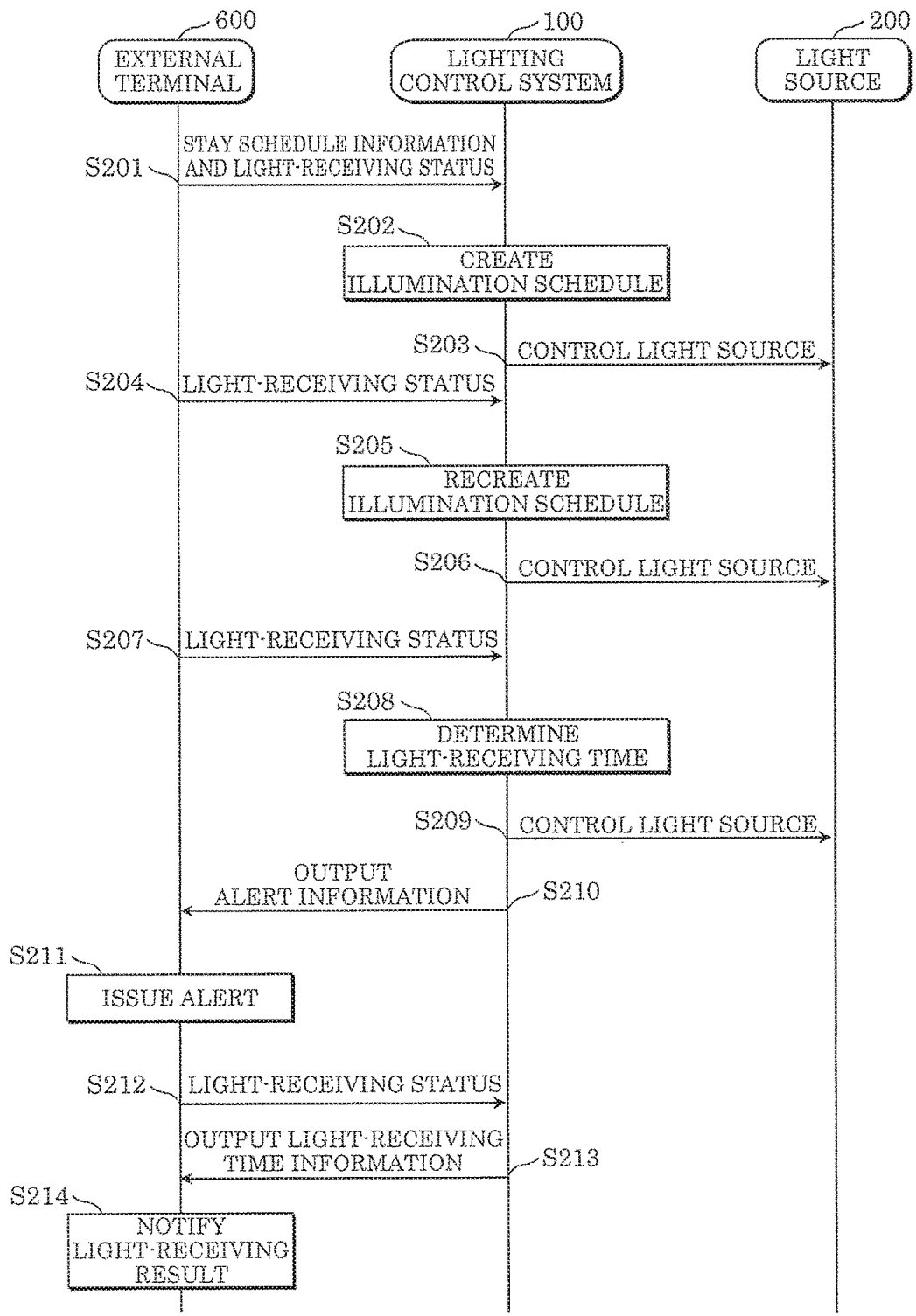

LIGHTING CONTROL SYSTEM, LIGHTING SYSTEM, AND LIGHTING CONTROL METHOD

CROSS REFERENCE TO RELATED APPLICATION

This application claims the benefit of priority of Japanese Patent Application Number 2017-154852 filed on Aug. 10, 2017, the entire content of which is hereby incorporated by reference.

BACKGROUND

1. Technical Field

The present disclosure relates to a lighting control system, a lighting system, and a lighting control method for use in controlling a light source that emits light to a space in which subjects stay.

2. Description of the Related Art

Conventionally, there is a known technique for controlling, when a light source such as a luminaire is caused to emit light, the light source according to a predetermined schedule (illumination schedule) (see, for example, Patent Literature (PTL) 1 (Japanese Unexamined Patent Application Publication No. 2013-246890)).

A lighting control system disclosed in PTL 1 sets, for a lighting device to be controlled, a specific day and a specific schedule to be followed on the specific day, and obtains current date information with predetermined timing. Further, the lighting control system disclosed in PTL 1 determines whether the obtained current data information corresponds to the specific day on which the specific schedule is followed. When the obtained current data information corresponds to the specific day, the lighting control system disclosed in PTL 1 causes the lighting device to emit light according to the specific schedule, and when the obtained current data information does not correspond to the specific day, the lighting control system causes the lighting device to emit light according to a preset basic schedule.

SUMMARY

In recent years, however, there is a known light therapy that controls the biological rhythm of a subject by emitting light equivalent to sunlight to the subject. For example, a subject stays in a facility in which a light source that emits light equivalent to sunlight is placed for a predetermined time, thereby being exposed to the light. As a result, the biological rhythm of the subject is controlled.

Here, from a standpoint of reducing the consumption energy of the light source, it is desirable to cause the light source to emit light to the subject while the subject is in the facility, and to emit no light when the subject is not in the facility. The same applies to a case in which subjects use the facility.

The present disclosure provides, for example, a lighting control system capable of efficiently emitting light to subjects.

A lighting control system according to one aspect of the present disclosure is a lighting control system that emits light to a space in which subjects stay. The lighting control system includes: a communication interface that obtains stay schedule information indicating scheduled periods in an operation period after a first time and before a second time later than the first time, the scheduled periods being periods during each of which a corresponding one of the subjects is to stay in the space; and a processor that creates an illumination schedule for causing the light source to emit the light, based on the stay schedule information, and causes the light source to emit the light according to the illumination schedule created. The creating unit creates, based on the stay schedule information, the illumination schedule for (i) allowing the subjects to achieve respective target light-receiving times that are predetermined and for which the subjects receive the light emitted by the light source, (ii) minimizing a time for which the light source emits the light, (iii) causing the light source to emit the light during a period including a scheduled period common to at least two of the subject, and (iv) causing the light source not to emit the light during a period including a scheduled period common to less than two of the subjects.

Moreover, a lighting system according to one aspect of the present disclosure includes the above lighting control system and the above light source.

Moreover, a lighting control method according to one aspect of the present disclosure is a lighting control method executed by a lighting control system that controls a light source that emits light to a space in which subjects stay. The lighting control method includes: obtaining, by a communication interface, stay schedule information indicating scheduled periods in an operation period after a first time and before a second time later than the first time, the scheduled periods being periods during each of which a corresponding one of the subjects is to stay in the space; creating, by a processor, an illumination schedule for causing the light source to emit the light, based on the stay schedule information obtained by the communication interface; and controlling, by the processor, the light source according to the illumination schedule created by the processor. In the creating, the processor creates, based on the stay schedule information, the illumination schedule for (i) allowing the subjects to achieve respective target light-receiving times that are predetermined and for which the subjects receive the light emitted by the light source, (ii) minimizing a time for which the light source emits the light, (iii) causing the light source to emit the light during a period including a scheduled period common to at least two of the subject, and (iv) causing the light source not to emit the light during a period including a scheduled period common to less than two of the subjects.

It should be noted that the present disclosure may be implemented as a program causing a computer to execute the steps included in the above lighting control method. Furthermore, the present disclosure may be implemented as a computer-readable recording medium having the program recorded thereon, such as a CD-ROM. In addition, the present disclosure may be implemented as information, data, or a signal representing the program. The program, information, data, or signal may be distributed via a communication network such as the Internet.

The lighting control system etc. of the present disclosure makes it possible to efficiently emit light to subjects.

BRIEF DESCRIPTION OF DRAWINGS

The figures depict one or more implementations in accordance with the present teaching, by way of examples only, not by way of limitations. In the figures, like reference numerals refer to the same or similar elements.

FIG. 5 is a sequence diagram indicating another example of a procedure from when the lighting control system according to the embodiment creates an illumination schedule to when the lighting control system causes the light source to emit light;

DETAILED DESCRIPTION OF THE EMBODIMENT

Hereinafter, a lighting control system etc. according to an embodiment will be described with reference to the drawings. It should be noted that the embodiment described below shows a generic or specific example. The numerical values, shapes, materials, structural elements, the arrangement and connection of the structural elements, steps, the processing order of the steps, etc. described in the following embodiment are mere examples, and are therefore not intended to limit the scope of the present disclosure. Furthermore, among the structural elements in the following embodiment, those not recited in any one of the independent claims representing the most generic concepts are described as optional structural elements.

It should be noted that the figures are schematic diagrams and are not necessarily precise illustrations. Furthermore, in the figures, substantially the same structural elements are assigned the same reference signs, and overlapping descriptions thereof may be omitted or simplified.

Embodiment

[Outline of Lighting System]

Figure 1:
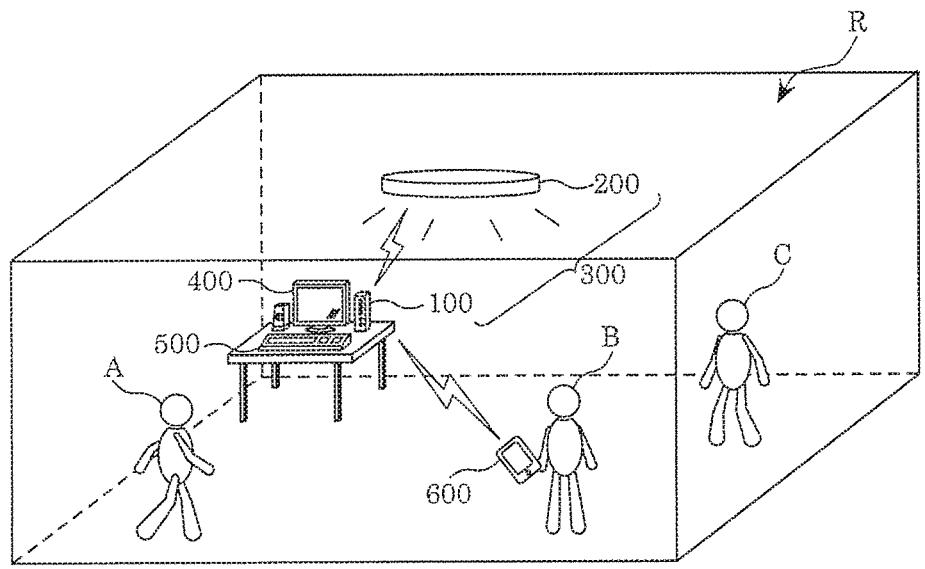
FIG. 1 is a diagram illustrating a lighting system according to an embodiment.

First, the following describes the outline of a lighting system according to an embodiment with reference to FIG. 1.

FIG. 1 is a diagram illustrating lighting system 300 according to the embodiment.

Lighting system 300 is a system that emits light to subjects A to C staying in space R such as a room. Specifically, lighting system 300 is used to control the biological rhythms of subjects A to C by emitting light to subjects A to C. For example, lighting system 300 causes light source 200 to emit light equivalent to sunlight to subjects A to C.

It should be noted that although FIG. 1 shows three persons, subject A, subject B, and subject C, the number of subjects to which the function of lighting system 300 is applied may be plural such as two or at least four. In what follows, the case of three persons, subject A, subject B, and subject C will be described.

Lighting system 300 includes: light source 200 that emits light; and lighting control system 100.

Light source 200 is a light source that emits light to subjects A to C. Light source 200 may be any light source capable of emitting light to subjects A to C, and a material, a configuration, etc. of light source 200 are not particularly limited. Light source 200 is a light-emitting diode (LED), a fluorescent light, a metal halide lamp, etc. Further, a color of light emitted by light source 200 is not particularly limited, and examples of the color include an electric lamp color, a white color, and a day white color. It should be noted that light emitted by light source 200 may be monochromatic light such as red light and blue light.

Lighting control system 100 is a control device that controls light source 200. Specifically, lighting control system 100 controls on and off of light source 200. In addition, lighting control system 100 creates an illumination schedule that is a schedule for turning on and off light source 200.

Lighting control system 100 obtains, for example, stay schedule information indicating what time subjects A to C will stay in space R, from subjects A to C. For example, subjects A to C output (transmit) their own stay schedule information to lighting control system 100 by operating input device 500 having an input mechanism such as a keyboard. It should be noted that a method for outputting, by subjects A to C, their own stay schedule information to lighting control system 100 is not particularly limited. For example, subjects A to C may output their own stay schedule information to lighting control system 100 by operating external terminal 600 such as a smartphone.

Lighting control system 100 creates the illumination schedule for turning on and off light source 200, based on the stay schedule information obtained from subjects A to C.

Notification device 400 is a display device for displaying an image etc. generated by lighting control system 100. Notification device 400 displays, for example, an image shown in FIG. 8C described later. Examples of notification device 400 include a liquid crystal display and an organic electroluminescent (EL) display. It should be noted that notification device 400 may not be a display device that displays an image, but may be, for example, a speaker that emits a sound.

[Configuration of Lighting System]

Figure 2:
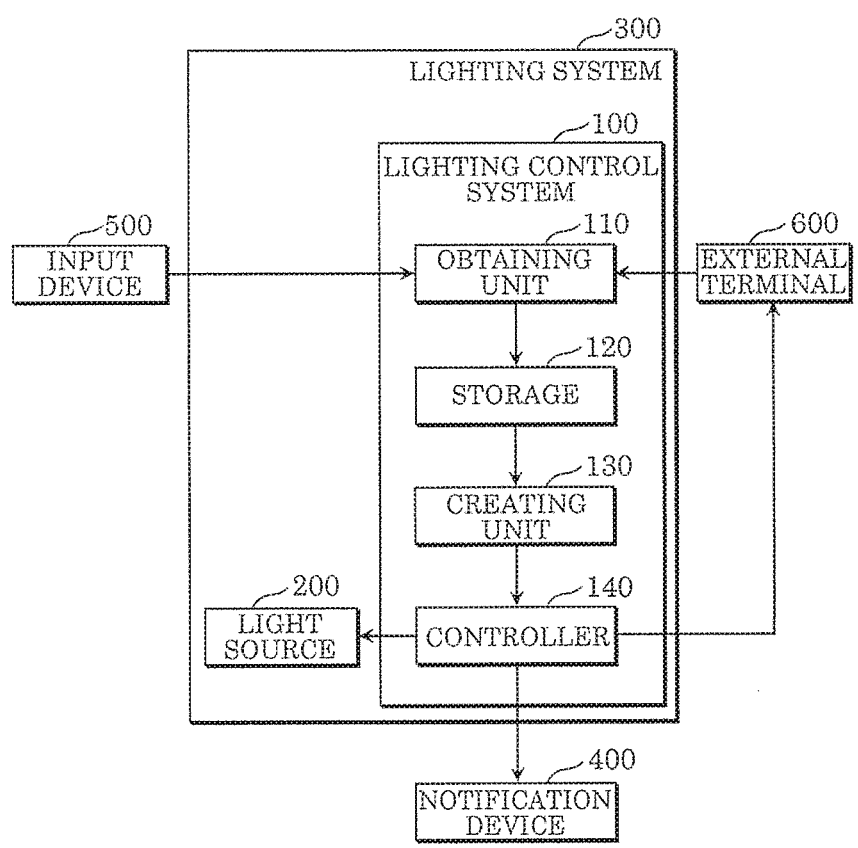
FIG. 2 is a block diagram illustrating a characteristic functional configuration of the lighting system according to the embodiment.

Next, the following describes a specific configuration of lighting system 300 with reference to FIG. 2.

FIG. 2 is a block diagram illustrating a characteristic functional configuration of lighting system 300 according to the embodiment.

Lighting system 300 includes light source 200 and lighting control system 100. Lighting control system 100 includes obtaining unit 110, storage 120, creating unit 130, and controller 140.

Obtaining unit 110 obtains stay schedule information which is scheduled periods during which subjects A to C stay in space R in an operation period after a first time and before a second time later than the first time. Here, the operation period indicates a time period during which light source 200 is allowed to emit light. For example, it is assumed that 8:00 and 16:00 are predetermined as a first time and a second time, respectively. In this case, lighting control system 100 creates an illumination schedule for causing light source 200 to emit no light during a time period of 0:00 to 8:00 and a time period of 16:00 to 24:00. It should be noted that the operation period may be set to any time period except nighttime, early morning, etc., and times set as the first time and the second time are not particularly limited.

Subjects A to C output, as the stay schedule information, what time between the first time and the second time subjects A to C will stay in space R to lighting control system 100 by operating input device 500, external terminal 600, etc. It should be noted that lighting control system 100 may be connected to the Internet. In this case, stay schedule information may be outputted from a personal computer used by any subject to lighting control system 100 via the Internet.

Obtaining unit 110 is, for example, a communication interface for obtaining stay schedule information outputted from input device 500, external terminal 600, etc. Storage 120 stores the stay schedule information obtained by obtaining unit 110.

Storage 120 is a memory that stores the stay schedule information of subjects A to C. Examples of storage 120 include a random-access memory (RAM), a hard disk drive (HDD), a solid-state device (SSD), and a flash memory.

Creating unit 130 reads the stay schedule information stored in storage 120, and creates an illumination schedule. Creating unit 130 creates, based on the stay schedule information, the illumination schedule for (i) allowing subjects A to C to achieve respective target light-receiving times that are predetermined and for which subjects A to C receive the light emitted by light source 200 and (ii) minimizing a time for which light source 200 emits the light. Specifically, creating unit 130 creates, based on the stay schedule information, the illumination schedule for (i) causing light source 200 to emit the light during a period including a scheduled period common to at least two of subjects A to C and (ii) causing light source 200 not to emit the light during a period including a scheduled period common to less than two of subjects A to C.

For example, creating unit 130 may create, based on the stay schedule information, the illumination schedule in which periods are included in descending order starting from a period including a scheduled period that is common to the highest number of subjects A to C among the scheduled periods of subjects A to C.

Moreover, for example, when at least two periods to be included in the illumination schedule are present, creating unit 130 may create the illumination schedule in which, out of the at least two periods, a period having the earliest time is included.

Creating unit 130 is implemented by, for example, a central processing unit (CPU) and a control program stored in storage 120 and executed by the CPU.

Controller 140 controls light source 200 according to the illumination schedule created by creating unit 130. Specifically, controller 140 performs switching between on and off of light source 200 according to the illumination schedule created by creating unit 130. Controller 140 is implemented by, for example, the CPU and the control program stored in storage 120 and executed by the CPU.

It should be noted that creating unit 130 and controller 140 may be implemented by one CPU or different CPUs. In addition, a control program executed by creating unit 130 and controller 140 may be stored in storage 120 or in a memory not shown which is separately included in lighting control system 100.

Moreover, creating unit 130 creates an illumination schedule on the basis of stay schedule information stored in storage 120 before the first time. Here, it is conceivable that any of subjects A to C may change a schedule for staying in space R. For this reason, when obtaining unit 110 obtains instruction information instructing a change of illumination schedule after the first time, creating unit 130 may recreate an illumination schedule on the basis of the instruction information. For example, a user of lighting control system 100 outputs the instruction information to lighting control system 100 after the first time by operating external terminal 600. The instruction information includes information about a time to change an illumination schedule, changed stay schedule information of subjects A to C when the stay schedule information of subjects A to C is changed, etc. Creating unit 130 recreates the illumination schedule on the basis of the instruction information obtained by obtaining unit 110.

Moreover, for example, creating unit 130 may recreate an illumination schedule at predetermined time intervals on the basis of the stay schedule information stored in storage 120. First, for example, creating unit 130 creates an illumination schedule on the basis of stay schedule information stored in storage 120 at 7:55 before 8:00, an example of the first time. Next, for example, creating unit 130 recreates an illumination schedule after 12:00 on the basis of stay schedule information stored again in storage 120 at 11:55.

Moreover, obtaining unit 110 may obtain a target light-receiving time that is a target time for emitting light to subjects A to C. Creating unit 130 may create an illumination schedule on the basis of the target light-receiving time of subjects A to C and stay schedule information of subjects A to C obtained by obtaining unit 110.

For example, subjects A to C may each output a light-receiving time as a light-receiving status to lighting control system 100 or output an amount of received light to lighting control system 100, by operating external terminal 600. In this case, for example, creating unit 130 may calculate the light-receiving time for which each of subjects A to C has received light, from the amount of received light. In addition, subjects A to C may each output a light-receiving status by operating external terminal 600, or lighting control system 100 may include a light sensor that each of subjects A to C carries, and external terminal 600 may automatically output, as the light-receiving status of each of subjects A to C, an amount of received light of the light sensor. For example, creating unit 130 may calculate, as a light-receiving status, an estimated light-receiving time for which light source 200 emits light to each of subjects A to C when each of subjects A to C stays in space R, from the amount of received light and an amount of light emitted per unit hour by light source 200.

For example, each of subjects A to C wears the light sensor. Obtaining unit 110 continuously obtains an amount of received light from the light sensor, and stores the amount of received light in storage 120. When light of 1000 lx is continuously received for one hour, the amount of received light is expressed as 1000 lx·hour. In this case, information (amount of received light) obtained by obtaining unit 110 is 1000 lx·hour. Further, obtaining unit 110 may obtain more than one amount of received light information.

It should be noted that a light-receiving status need not be an amount of received light. The light-receiving status may be information such as how long a subject has stayed outdoors or indoors. Lighting control system 100 may estimate an amount of received light of the subject on the basis of the information. For example, the subject carries a device having a global positioning system (GPS) function. Lighting control system 100 may obtain, from the device, a time for which the subject has stayed indoors and a time for which the subject has stayed outdoors, determine in advance that amounts of received light of the subject outdoors and indoors are, for example, 10000 lx and 300 lx, respectively, relative to a stay time, and estimate an amount of received light.

Moreover, lighting control system 100 may further obtain, as a light-receiving status, information such as weather and a season, and estimate an amount of received light on the basis of the information. Lighting control system 100 may estimate an amount of received light of a subject, assuming that, for example, amounts of received light in an outdoor place and an indoor place on a rainy day are 5000 lx and 150 lx, respectively, an amount of received light in summer is 1.5 times greater than that in spring or autumn, and an amount of received light in winter is 0.8 times greater than that in spring or autumn.

Moreover, the light-receiving status may be not only stay information about stay in an indoor place, an outdoor place, etc. by a subject but also stay information about stay in space R. The subject carries, for example, a radio frequency (RF) tag. Lighting control system 100 may obtain stay information indicating whether the subject is in space R by communicating with the RF tag. In addition, lighting control system 100 may include a camera, obtain a video from the camera capturing space R, and obtain stay information indicating whether the subject is in space R by analyzing the video. Further, for example, the subject or another person may output an amount of received light to lighting control system 100 by operating external terminal 600 etc.

Moreover, the light-receiving status may be set not with an amount of received light but with a light-receiving time. In general, a subject is required to have an amount of received light of 5000 lx·hour per day. For this reason, when light source 200 is placed in space R such that light emitted by light source 200 causes the face illuminance of the subject to be 1000 lx, the subject is required to have a light-receiving time of five hours per day. In addition, when light source 200 is placed in space R such that light emitted by light source 200 causes the face illuminance of the subject to be 1700 lx, the subject is required to have a light-receiving time of three hours per day. In such a manner, a light-receiving time calculated from a target light-receiving time and a light-receiving status may be appropriately set on the basis of an amount of light emitted by light source 200, the placement of light source 200 in space R, etc. The embodiment will be described assuming that a light-receiving time is obtained as a light-receiving status.

It should be noted that the target light-receiving time may be determined in any manner. For example, lighting control system 100 may include a pressure sensor, obtain a change of pressure from the pressure sensor disposed on a bed of a subject, and estimate a sleep time of the subject. Lighting control system 100 may calculate a target light-receiving time from the estimated sleep time of the subject. Lighting control system 100 calculates, for example, a daily sleep time of the subject. When lighting control system 100 determines that a sleep time of the subject is shorter, lighting control system 100 may set a target light-receiving time longer than a normal target light-receiving time.

Moreover, creating unit 130 may create an illumination schedule for allowing the largest number of subjects among subjects A to C to achieve at least the target light-receiving time, based on the scheduled stay information and the target light-receiving time of each of subjects A to C.

Furthermore, creating unit 130 may determine whether subjects A to C will achieve at least the target light-receiving time, based on the stay schedule information and the target light-receiving time. In this case, when creating unit 130 determines that an underachieving subject who will not achieve at least the target light-receiving time is present among subjects A to C, controller 140 may output alert information indicating the presence of the underachieving subject. Examples of the alert information include image information and audio information. For example, controller 140 outputs the alert information to notification device 400 and external terminal 600. Notification device 400 and external terminal 600 output an image, audio, etc. on the basis of the obtained alert information.

Moreover, obtaining unit 110 may obtain a light-receiving status from each of subjects A to C. For example, it is conceivable that subjects A to C receive sunlight in addition to light from light source 200 while staying in space R. Creating unit 130 may correct a target light-receiving time of subjects A to C using the light-receiving statuses indicating amounts of light received by subjects A to C or light-receiving times for which a predetermined amount of light is received, and create an illumination schedule. In other words, obtaining unit 110 may obtain the light-receiving status after the first time and until a third time before the second time of each of subjects A to C. In this case, creating unit 130 may determine whether subjects A to C will achieve at least the target light-receiving time by comparing the light-receiving statuses and the target light-receiving time before the second time. When creating unit 130 determines that an underachieving subject who will not achieve at least the target light-receiving time is present among subjects A to C, creating unit 130 may recreate an illumination schedule after the third time.

It should be noted that lighting control system 100 may include a timer such as a real time clock (RTC) to measure a time. Creating unit 130 may obtain the current time from the timer. Alternatively, lighting control system 100 may obtain the current time from external terminal 600 etc. through communication.

Moreover, when creating unit 130 determines that an underachieving subject who will not achieve at least the target light-receiving time is present at the third time, controller 140 may output alert information indicating the presence of the underachieving subject, to notification device 400 and external terminal 600.

Furthermore, obtaining unit 110 may obtain a light-receiving status after the third time and until a fourth time before the second time of each of subjects. The fourth time is a time at which the remaining time of an operation period scheduled for a day is running out, such as one hour before the second time.

Moreover, creating unit 130 may determine whether subjects A to C will achieve at least the target light-receiving time by comparing the light-receiving statuses and the target light-receiving time before the second time. In this case, when creating unit 130 determines that an underachieving subject who will not achieve at least the target light-receiving time is present among subjects A to C, controller 140 may output alert information indicating the presence of the underachieving subject and cause light source 200 to emit light until the second time. In the case where the remaining time of an operation period scheduled for a day is running out, when the underachieving subject who will not achieve at least the target light-receiving time is present, lighting control system 100 causes light source 200 to keep emitting light until the second time.

Moreover, obtaining unit 110 may obtain a light-receiving status until the second time of each of subjects A to C. In this case, creating unit 130 may determine whether each of subjects A to C will achieve at least the target light-receiving time. In addition, controller 140 may output result information indicating the result of the determination by creating unit 130. In other words, controller 140 may notify the result of a daily light-receiving status of each of subjects A to C to a corresponding one of subjects A to C. Examples of the result information include image information and audio information. For example, controller 140 outputs the result information to notification device 400 and external terminal 600. Notification device 400 and external terminal 600 that have obtained the result information output an image, audio, etc on the basis of the result information.

[Operational Procedure of Lighting System]

Figure 3:
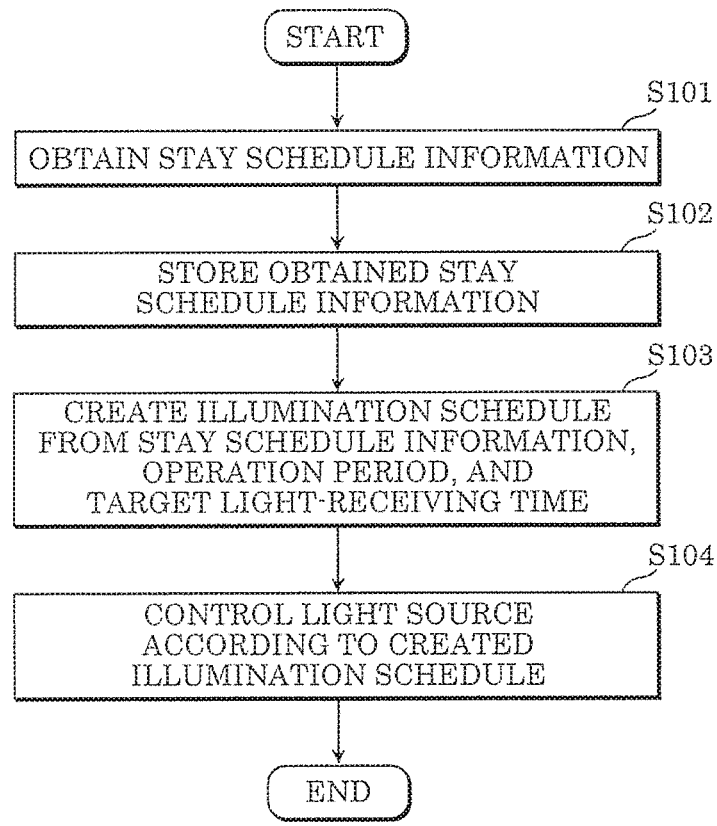
FIG. 3 is a flow chart indicating an example of a procedure from when a lighting control system according to the embodiment creates an illumination schedule to when the lighting control system causes a light source to emit light.
Figure 4:
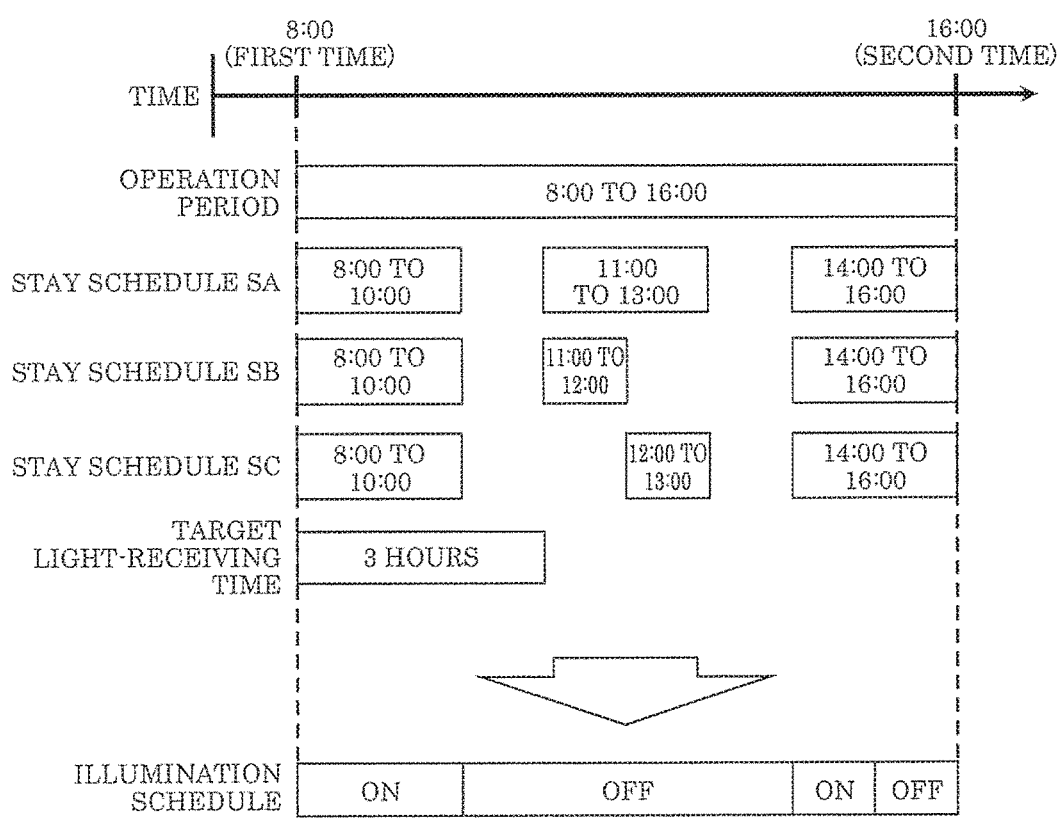
FIG. 4 is a diagram illustrating an illumination schedule created by the lighting system according to the embodiment.

Next, the following describes a specific operational procedure by which lighting control system 100 creates an illumination schedule and causes light source 200 to emit light, with reference to FIG. 3 and FIG. 4.

FIG. 3 is a flow chart indicating a procedure from when lighting control system 100 according to the embodiment creates an illumination schedule to when lighting control system 100 causes light source 200 to emit light. FIG. 4 is a diagram illustrating an illumination schedule created by lighting system 100 according to the embodiment.

As shown in FIG. 3, obtaining unit 110 obtains stay schedule information from subjects A to C (step S101).

Next, obtaining unit 110 stores the obtained stay schedule information in storage 120 (step S102).

Next, creating unit 130 creates an illumination schedule from the stay schedule information stored in storage 120, an operation period, and a target light-receiving time (step S103).

Next, controller 140 controls light source 200 according to the illumination schedule created by creating unit 130 (step S104).

As shown in FIG. 4, for example, it is assumed that obtaining unit 110 obtains stay schedule information SA from subject A, stay schedule information SB from subject B, and stay schedule information SC from subject C. It should be noted that in FIG. 4, it is assumed that a time common to subjects A to C is preset as a target light-receiving time of each of subjects A to C. For example, in FIG. 4, three hours are set as the target light-receiving time of subjects A to C. Moreover, in FIG. 4, an operation period is preset and is assumed to range from, for example, 8:00 to 16:00. To put it differently, in this case, a first time and a second time are 8:00 and 16:00, respectively.

First, creating unit 130 extracts, from stay schedule information SA to SC, 8:00 to 10:00 and 14:00 to 16:00 that are periods with many visitors. Moreover, creating unit 130 determines an illumination time of three hours on the basis of 8:00 to 10:00 and 14:00 to 16:00 because the target light-receiving time of subjects A to C is three hours. For example, creating unit 130 creates an illumination schedule for a total of three hours consisting of two hours from 8:00 to 10:00, the earlier period, and one hour from 14:00 to 15:00. Controller 140 causes light source 200 to emit light (ON) from 8:00 to 10:00 and from 14:00 to 15:00 and to stop emitting light (OFF) in any period other than these periods, according to the illumination schedule created by creating unit 130.

It should be noted that the target light-receiving time and the operation period may be determined in any manner. For example, obtaining unit 110 may obtain an operation period and a target light-receiving time of each of subjects A to C in step S101 shown in FIG. 3. In this case, creating unit 130 may create an illumination schedule on the basis of the operation period and the target light-receiving time of each of subjects A to C obtained by obtaining unit 110. It should be noted that in the following description, an example will be given in which an operation period is preset to have 8:00 as the first time and 16:00 as the second time.

Next, the following describes another example of a specific operational procedure by which lighting control system 100 creates an illumination schedule and causes light source 200 to emit light, with reference to FIG. 5 to FIG. 9B.

FIG. 5 is a sequence diagram indicating another example of a procedure from when lighting control system 100 according to the embodiment creates an illumination schedule to when lighting control system 100 causes light source 200 to emit light. It should be noted that FIG. 5 to FIG. 9B illustrate a case in which subjects A to C output their own stay schedule information and light-receiving statuses to lighting control system 100 by operating external terminal 600. Further, in FIG. 5 to FIG. 9B, an operation period is preset to have 8:00 as the firrst time and 16:00 as the second time.

Subjects A to C output their own stay schedule information and light-receiving statuses to lighting control system 100 by the first time by operating external terminal 600 (step S201). Here, the light-receiving statuses mean light-receiving times for which subjects A to C have received a predetermined amount of light. For example, it is assumed that subjects A to C have received light such as sunlight before the first time. In such a case, subjects A to C output, as the light-receiving statuses, the light-receiving times for which subjects A to C have received the predetermined amount of light, to lighting control system 100.

Next, lighting control system 100 obtains from external terminal 600 the stay schedule information and light-receiving statuses of subjects A to C, and stores the stay schedule information and light-receiving statuses of subjects A to C. Lighting control system 100 creates an illumination schedule from the stay schedule information and light-receiving statuses of subjects A to C stored by the first time (step S202).

Figure 6A:
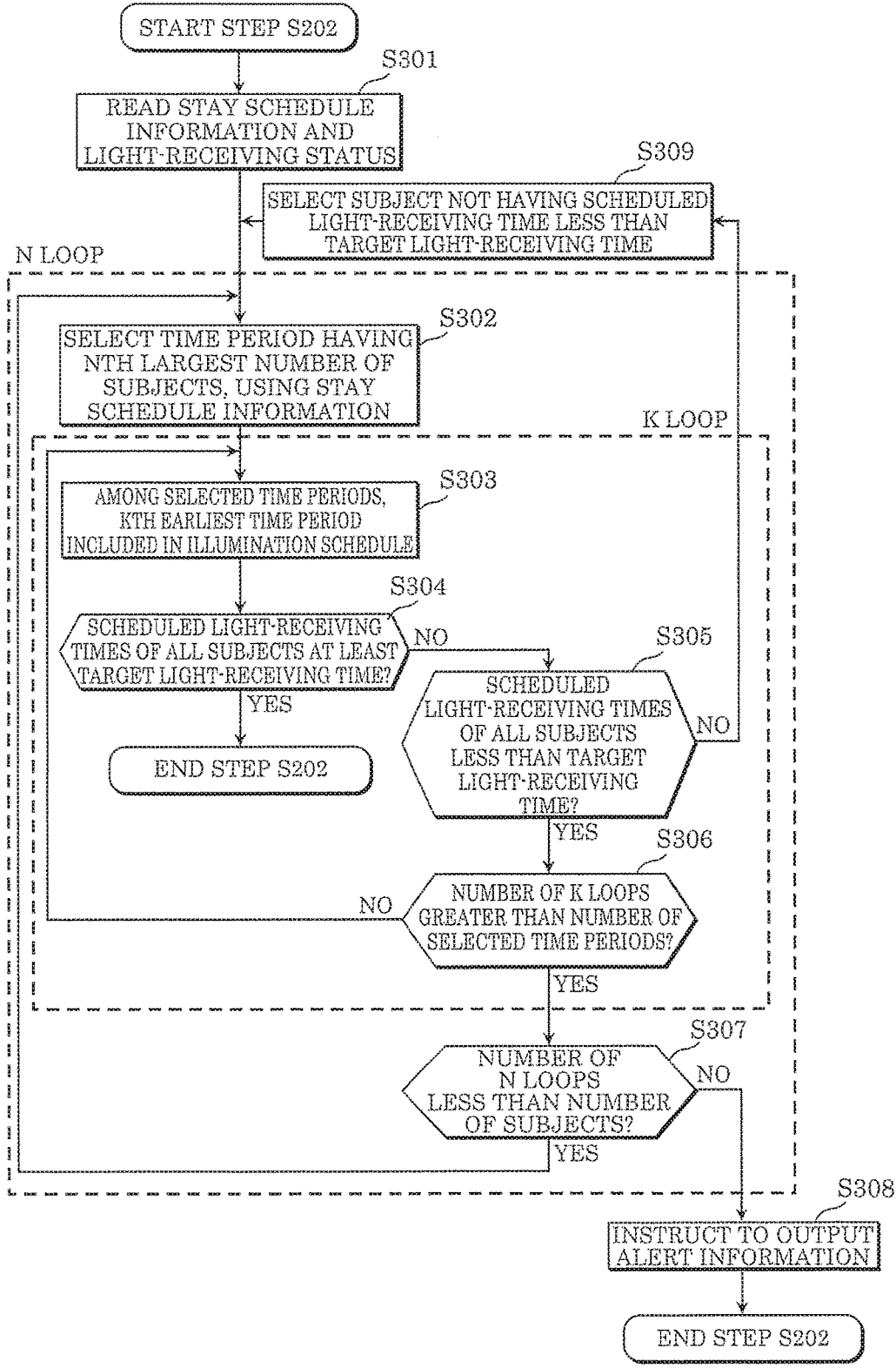
FIG. 6A is a flow chart indicating a procedure by which the lighting control system according to the embodiment creates an illumination schedule.
Figure 6B:
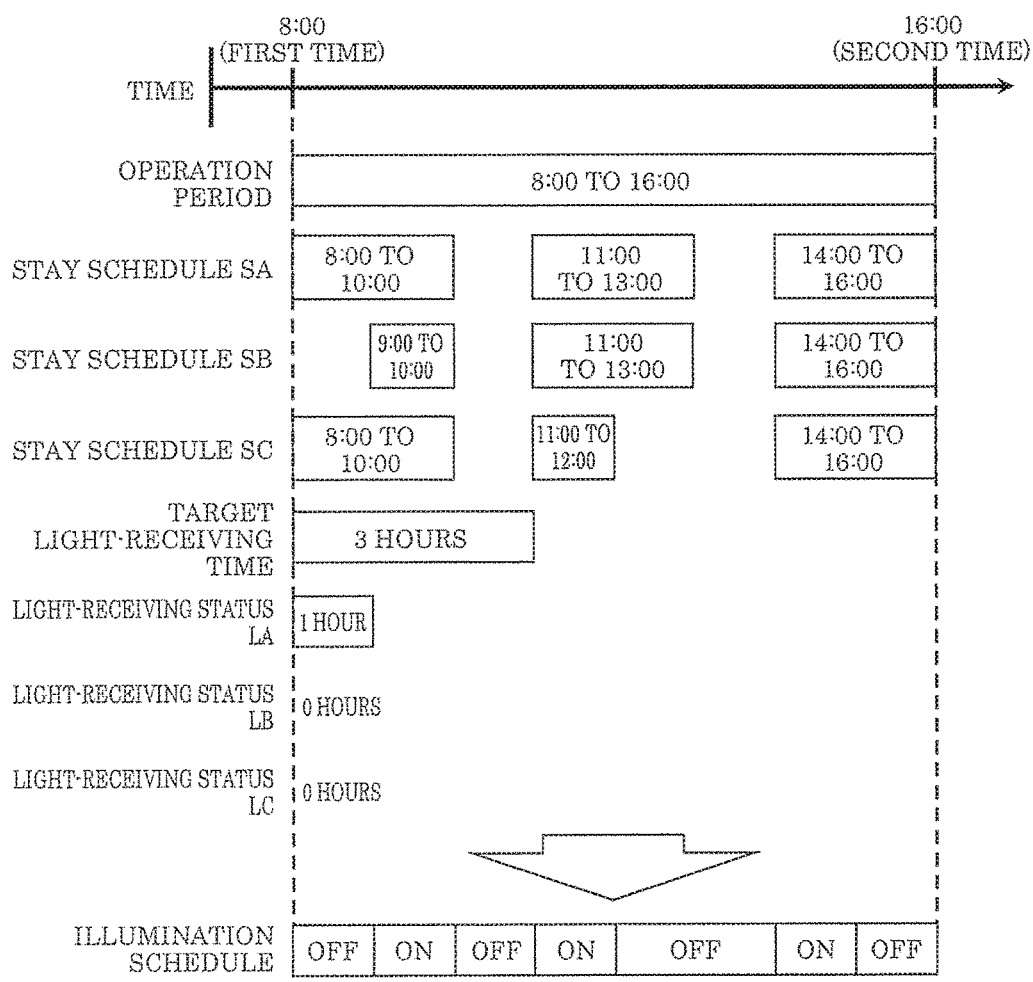
FIG. 6B is a diagram illustrating an illumination schedule that the lighting control system according to the embodiment creates by a first time.

FIG. 6A is a flow chart indicating a procedure by which lighting control system 100 according to the embodiment creates an illumination schedule. Specifically, FIG. 6A is a flow chart illustrating the details of step S202 shown in FIG. 5. FIG. 6B is a diagram illustrating an illumination schedule that lighting control system 100 according to the embodiment creates by the first time. Specifically, FIG. 6B is a diagram illustrating stay schedule information and light-receiving statuses of subjects A to C and the illumination schedule created by creating unit 130 according to the flow chart shown in FIG. 6A.

As shown in FIG. 6A, creating unit 130 reads the stay schedule information and light-receiving statuses of subjects A to C stored in storage 120 (step S301). Specifically, as shown in FIG. 6B, in step S301, creating unit 130 reads from storage 120 stay schedule information SA and light-receiving status LA of subject A, stay schedule information SB and light-receiving status LB of subject B, and stay schedule information SC and light-receiving status LC of subject C, and a target light-receiving time. It should be noted that in step S301, creating unit 130 calculates that a remaining light-receiving time of subject A is two hours, from light-receiving status LA of subject A and the target light-receiving time.

Referring to FIG. 6A again, after step S301, creating unit 130 selects a time period having an Nth largest number of subjects on the basis of stay schedule information SA to SC of subjects A to C read from storage 120 (step S302). Here, the number of times steps from step S302 to step S307 to be described later (N loop) are executed is applied to "N" in "Nth." In other words, when step S302 is executed for the first time, creating unit 130 selects, in step S302, a time period having the largest number of subjects on the basis of stay schedule information SA to SC of subjects A to C read from storage 120. When step S302 is executed for the second time, creating unit 130 selects, in step S302, a time period having the second largest number of subjects on the basis of stay schedule information SA to SC of subjects A to C read from storage 120. As shown in FIG. 6B, in step S302, creating unit 130 selects 9:00 to 10:00, 11:00 to 12:00, and 14:00 to 16:00 that are time periods in which all subjects A to C are scheduled to stay in space R. It should be noted that a unit time of a time period selected by creating unit 130 may be set in any manner. For example, it is assumed that one hour is preset as the unit time. In this case, in step S302, creating unit 130 selects four time periods of 9:00 to 10:00, 11:00 to 12:00, 14:00 to 15:00, and 15:00 to 16:00 in which all subjects A to C are scheduled to stay in space R.

Referring to FIG. 6A again, after step S302, creating unit 130 includes, from among the time periods selected in step S302, a Kth earliest time period in the illumination schedule (step S303). Here, the number of times steps from step S303 to step S306 to be described later (K loop) are executed is applied to "K" in "Kth." In other words, when step S303 is executed for the first time, creating unit 130 includes, from among the time periods selected in step S302, the earliest time period in the illumination schedule in step S303. When step S303 is executed for the second time, creating unit 130 includes, from among the time periods selected in step S302, the second earliest time period in the illumination schedule in step S303. Creating unit 130 includes, from among the four time periods of 9:00 to 10:00, 11:00 to 12:00, 14:00 to 15:00, and 15:00 to 16:00, 9:00 to 10:00 in the illumination schedule in step S303.

Next, creating unit 130 determines whether scheduled light-receiving times of all subjects A to C are greater than or equal to the target light-receiving time, based on the created illumination schedule (step S304). When creating unit 130 determines that the scheduled light-receiving times of all subjects A to C are greater than or equal to the target light-receiving time, based on the created illumination schedule (Yes in step S304), creating unit 130 finishes creating the illumination schedule, and step S202 is ended.

In contrast, when creating unit 130 determines that any of the scheduled light-receiving times of subjects A to C is not greater than or equal to the target light-receiving time, based on the created illumination schedule (No in step S304), creating unit 130 determines whether all subjects A to C have achieved the target light-receiving time (step S305). When creating unit 130 determines that any of subjects A to C has achieved at least the target light-receiving time (No in step S305), creating unit 130 selects only a subject having not achieved at least the target light-receiving time on the basis of the created illumination schedule, and processing returns to step S302.

It should be noted that when determination of No is made in step S305, creating unit 130 resets the numbers of times the N loop and the K loop are executed, and recounts the N loop and the K loop.

In contrast, when creating unit 130 determines that all subjects A to C have not achieved at least the target light-receiving time (Yes in step S305), creating unit 130 determines whether the number of K loops is greater than the number of the selected time periods (step S306). When creating unit 130 determines that the number of the K loops is not greater than the number of the selected time periods (No in step S306), processing returns to step S303 (K loop). In other words, creating unit 130 determines whether the number of the time periods selected in step S302 is greater than the number of the K loops in step S306.

When creating unit 130 determines that the number of the K loops is greater than the number of the selected time periods (Yes in step S306), creating unit 130 determines whether the number of N loops is less than the number of subjects A to C (step S307). When creating unit 130 determines that the number of the N loops is less than the number of subjects A to C (Yes in step S307), processing returns to step S302 (N loop).

In contrast, when creating unit 130 determines that the number of the N loops is not less than the number of subjects A to C (No in step S307), creating unit 130 instructs controller 140 to output, to external terminal 600, notification device 400, etc., alert information that is information indicating the presence of an underachieving subject who cannot receive light for a time greater than or equal to the target light-receiving time according to the created illumination schedule (have not achieved at least the target light-receiving time) (step S308), and step S202 is ended.

It should be noted that when creating unit 130 creates an illumination schedule, controller 140 may notify, for example, the illumination schedule created by creating unit 130 to external terminal 600 used by subjects A to C.

This allows subjects A to C to know time periods in each of which light source 200 emits light, and thus subjects A to C can go to space R with an appropriate timing when light source 200 emits the light.

As shown in FIG. 6B, creating unit 130 executes the processing according to the flow chart shown in FIG. 6A, and creates the illumination schedule for controller 140 to cause light source 200 to emit light from 9:00 to 10:00, 11:00 to 12:00, and 14:00 to 15:00.

Referring to FIG. 5 again, controller 140 causes light source 200 to emit light according to the illumination schedule created in step S202 by creating unit 130 (step S203).

After creating unit 130 created the illumination schedule in step S202 (i.e., after the first time), subjects A to C may output their own light-receiving statuses to lighting control system 100 by operating external terminal 600, input device 500, etc. (step S204). When lighting control system 100 obtains a light-receiving status, lighting control system 100 stores the light-receiving status. When lighting control system 100 already obtained a light-receiving status, lighting control system 100 replaces a stored light-receiving status with the obtained light-receiving status.

Creating unit 130 may recreate an illumination schedule by the third time that is preset, based on light-receiving statuses stored in storage 120. It should be noted that any user of lighting control system 100 may set the third time. The embodiment will be described assuming that the third time is preset to 12:00.

Figure 7A:
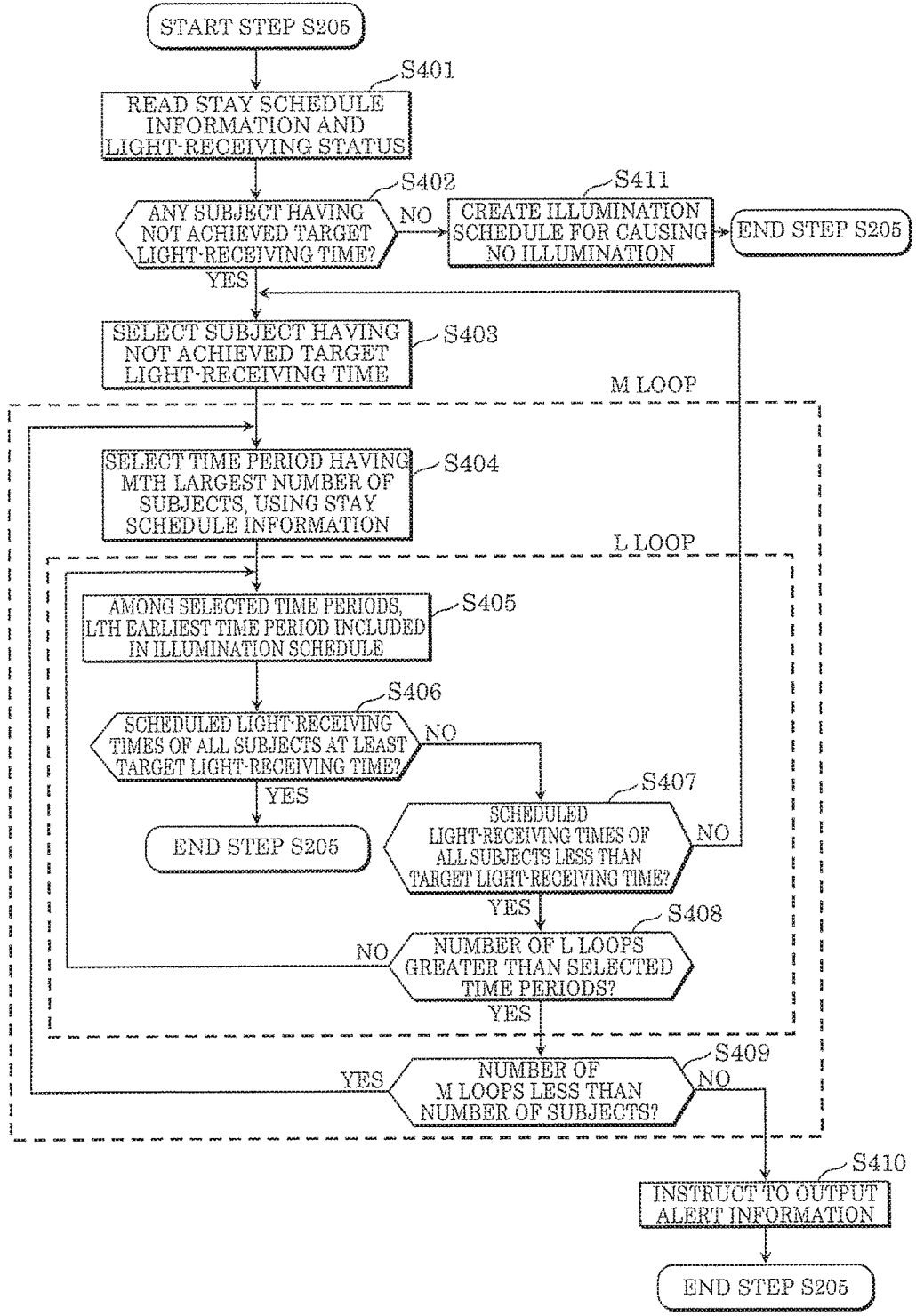
FIG. 7A is a flow chart indicating a procedure by which the lighting control system according to the embodiment recreates an illumination schedule.
Figure 7B:
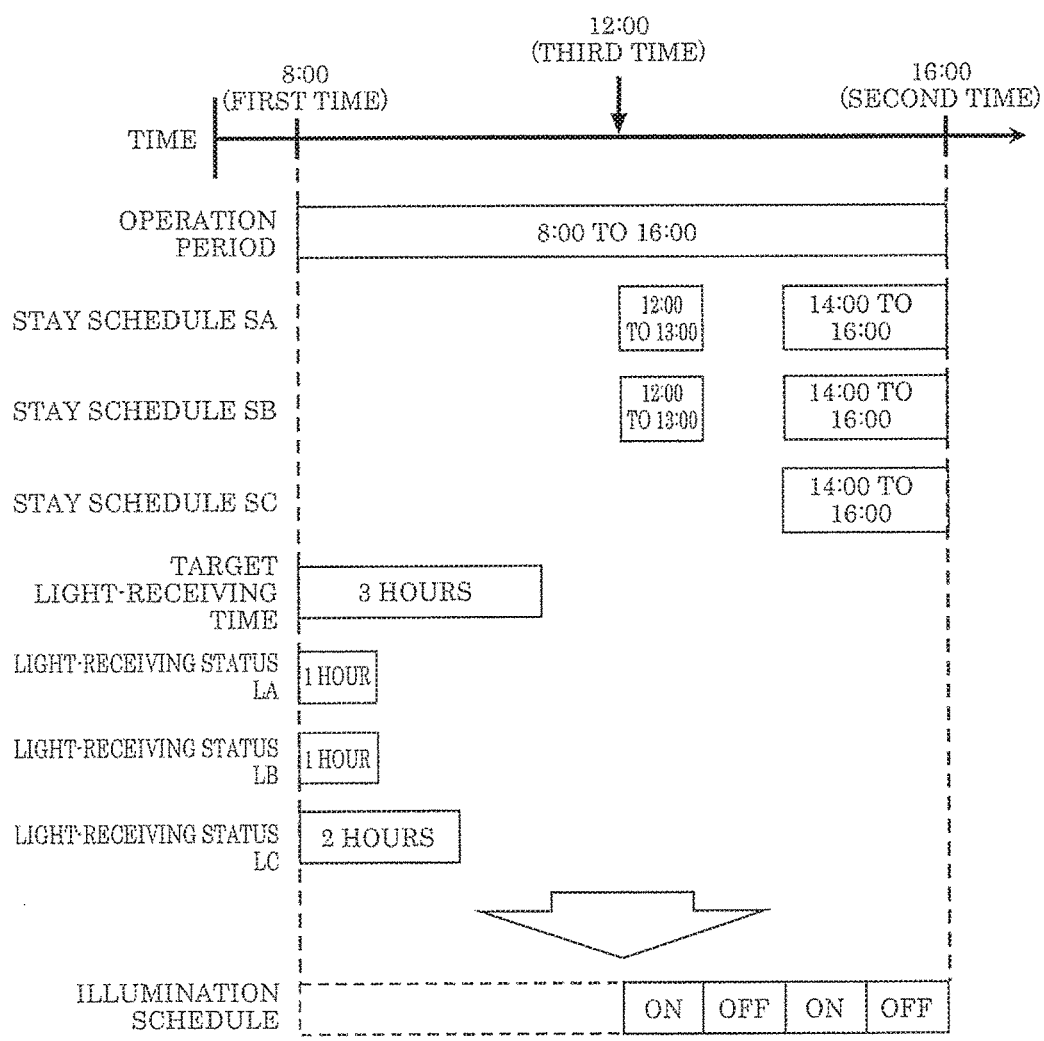
FIG. 7B is a diagram illustrating an illumination schedule that the lighting control system according to the embodiment creates by a third time.

FIG. 7A is a flow chart indicating a procedure by which lighting control system 100 according to the embodiment recreates an illumination schedule. Specifically, FIG. 7A is a flow chart illustrating the details of step S205 shown in FIG. 5. FIG. 7B is a diagram illustrating an illumination schedule that lighting control system 100 according to the embodiment creates by the third time. Specifically, FIG. 7B is a diagram illustrating stay schedule information and light-receiving statuses of subjects A to C and the illumination schedule recreated by creating unit 130 according to the flow chart shown in FIG. 7A.

As shown in FIG. 7A, creating unit 130 reads the stay schedule information and light-receiving statuses of subjects A to C stored in storage 120 (step S401). Specifically, in step S401, creating unit 130 reads from storage 120 stay schedule information SA and light-receiving status LA of subject A, stay schedule information SB and light-receiving status LB of subject B, and stay schedule information SC and light-receiving status LC of subject C, and a target light-receiving time that are shown in FIG. 7B. For example, as shown in FIG. 7B, it is assumed that by the third time, a light-receiving time (light-receiving status LA) of subject A is one hour, a light-receiving time (light-receiving status LB) of subject B is one hour, and a light-receiving time (light-receiving status LC) of subject C is two hours. In other words, it is assumed that subject A and subject B have not received light from light source 200 as indicated by stay schedule information SA and stay schedule information SB that lighting control system 100 obtained by the first time. In such a case, the illumination schedule shown in FIG. 6B does not allow subject B to receive light for a time greater than or equal to the target light-receiving time. Lighting control system 100 recreates an illumination schedule on the basis of newly obtained light-receiving statuses LA to LC.

Referring to FIG. 7A again, creating unit 130 determines whether a subject having a light-receiving time less than the target light-receiving time is present (step S402). When creating unit 130 determines that the subject having the light-receiving time less than the target light-receiving time is not present (No in step S402), creating unit 130 creates an illumination schedule for causing light source 200 to emit no light after the third time (step S411), and step S205 is ended.

In contrast, when creating unit 130 determines that the subject having the light-receiving time less than the target light-receiving time is present (Yes in step S402), creating unit 130 selects the subject having not achieved the target light-receiving time (step S403), and steps subsequent to step S403 are executed.

Next, creating unit 130 selects a time period having an Mth largest number of subjects on the basis of stay schedule information SA to SC of subjects A to C read from storage 120 (step S404). Here, the number of times steps from step S404 to step S409 to be described later (M loop) are executed is applied to "M" in "Mth." In other words, when step S404 is executed for the first time, creating unit 130 selects, in step S404, a time period having the largest number of subjects on the basis of stay schedule information SA to SC of subjects A to C read from storage 120. When step S404 is executed for the second time, creating unit 130 selects, in step S404, a time period having the second largest number of subjects on the basis of stay schedule information SA to SC of subjects A to C read from storage 120. As shown in FIG. 7B, in step S404, creating unit 130 selects two time periods of 14:00 to 15:00 and 15:00 to 16:00 in which all subjects A to C are scheduled to stay in space R.

Referring to FIG. 7A again, after step S404, creating unit 130 includes, from among the time periods selected in step S404, an Lth earliest time period in the illumination schedule (step S405). Here, the number of times steps from step S405 to step S408 to be described later (L loop) are executed is applied to "L" in "Lth." In other words, when step S405 is executed for the first time, creating unit 130 includes, from among the time periods selected in step S404, the earliest time period in the illumination schedule in step S405. When step S405 is executed for the second time, creating unit 130 includes, from among the time periods selected in step S404, the second earliest time period in the illumination schedule in step S405. Creating unit 130 includes, out of the two time periods of 14:00 to 15:00 and 15:00 to 16:00, 14:00 to 15:00 in the illumination schedule in step S405.

Next, creating unit 130 determines whether scheduled light-receiving times of all subjects A to C are greater than or equal to the target light-receiving time, based on the created illumination schedule (step S406). When creating unit 130 determines that the scheduled light-receiving times of all subjects A to C are greater than or equal to the target light-receiving time, based on the created illumination schedule (Yes in step S406), creating unit 130 finishes creating the illumination schedule.

In contrast, when creating unit 130 determines that any of the scheduled light-receiving times of subjects A to C is not greater than or equal to the target light-receiving time, based on the created illumination schedule (No in step S406), creating unit 130 determines whether all subjects A to C have achieved the target light-receiving time (step S407). When creating unit 130 determines that any of subjects A to C has achieved at least the target light-receiving time (No in step S407), processing returns to step S403. In other words, in step S403 after determination No is made in step S407, creating unit 130 selects subject A and subject B who have not achieved at least the target light-receiving time, and the subsequent steps are executed. For this reason, creating unit 130 selects three time periods of 12:00 to 13:00, 14:00 to 15:00, and 15:00 to 16:00 in next step S404.

It should be noted that when the determination of No is made in step S407, creating unit 130 resets the numbers of M loops and L loops, and recounts the M loop and the L loop.

In contrast, when creating unit 130 determines that all subjects A to C have not achieved at least the target light-receiving time (Yes in step S407), creating unit 130 determines whether the number of the L loops is greater than the number of the selected time periods (step S408). When creating unit 130 determines that the number of the L loops is not greater than the number of the selected time periods (No in step S408), processing returns to step S405 (L loop). In other words, creating unit 130 determines whether the number of the time periods selected in step S404 is greater than the number of the L loops in step S408.

When creating unit 130 determines that the number of the L loops is greater than the number of the selected time periods (Yes in step S408), creating unit 130 determines whether the number of the M loops is less than the number of subjects A to C (step S409). When creating unit 130 determines that the number of the M loops is less than the number of subjects A to C (Yes in step S409), processing returns to step S404 (M loop).

In contrast, when creating unit 130 determines that the number of the M loops is not less than the number of subjects A to C (No in step S409), creating unit 130 instructs controller 140 to output, to external terminal 600, notification device 400, etc., alert information that is information indicating the presence of an underachieving subject who has not achieved at least the target light-receiving time according to the created illumination schedule (step S410), and step S205 is ended.

As shown in FIG. 7B, creating unit 130 executes the processing according to the flow chart shown in FIG. 7A, and recreates the illumination schedule for controller 140 to cause light source 200 to emit light from 12:00 to 13:00 and 14:00 to 15:00.

Referring to FIG. 5 again, after step S205, lighting control system 100 controls light source 200 according to the created illumination schedule (step S206).

Next, subjects A to C output their own light-receiving statuses to lighting control system 100 by the fourth time by operating external terminal 600 (step S207).

Lighting control system 100 obtains from external terminal 600 the light-receiving statuses of subjects A to C, and stores the light-receiving statuses of subjects A to C. Lighting control system 100 determines whether all subjects A to C have achieved at least the target light-receiving time by the fourth time according to the illumination schedule, based on the stored light-receiving statuses of subjects A to C (step S208).

Figure 8A:
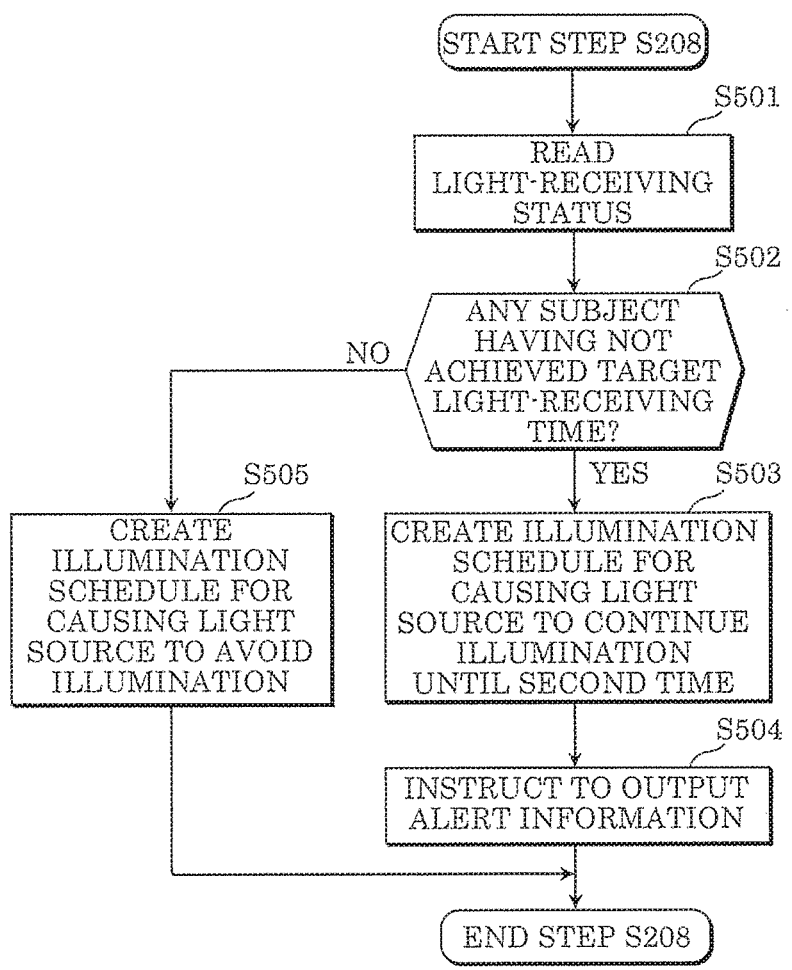
FIG. 8A is a flow chart indicating a procedure by which the lighting control system according to the embodiment determines light-receiving statuses of subjects.

FIG. 8A is a flow chart indicating a procedure by which lighting control system 100 according to the embodiment determines light-receiving statuses of subjects A to C.

When the current time reaches the fourth time, creating unit 130 reads the light-receiving statuses of subjects A to C stored in storage 120 (step S501). The fourth time may be preset or may be set in any manner by a user of lighting control system 100. The embodiment will be described assuming that the fourth time is preset to 15:00.

Next, creating unit 130 determines whether any of subjects A to C who has not achieved the target light-receiving time is present, based on the light-receiving statuses of subjects A to C read from storage 120 (step S502).

When creating unit 130 determines that any of subjects A to B who has not achieved the target light-receiving time is present (Yes in step S502), creating unit 130 creates an illumination schedule for causing light source 200 to keep emitting light until the second time (step S503). In addition, creating unit 130 instructs controller 140 to output alert information (step S504).

In contrast, when creating unit 130 determines that any of subjects A to B who has not achieved the target light-receiving time is not present (No in step S502), creating unit 130 creates an illumination schedule for causing light source 200 to emit no light after the fourth time (step S505).

Figure 8B:
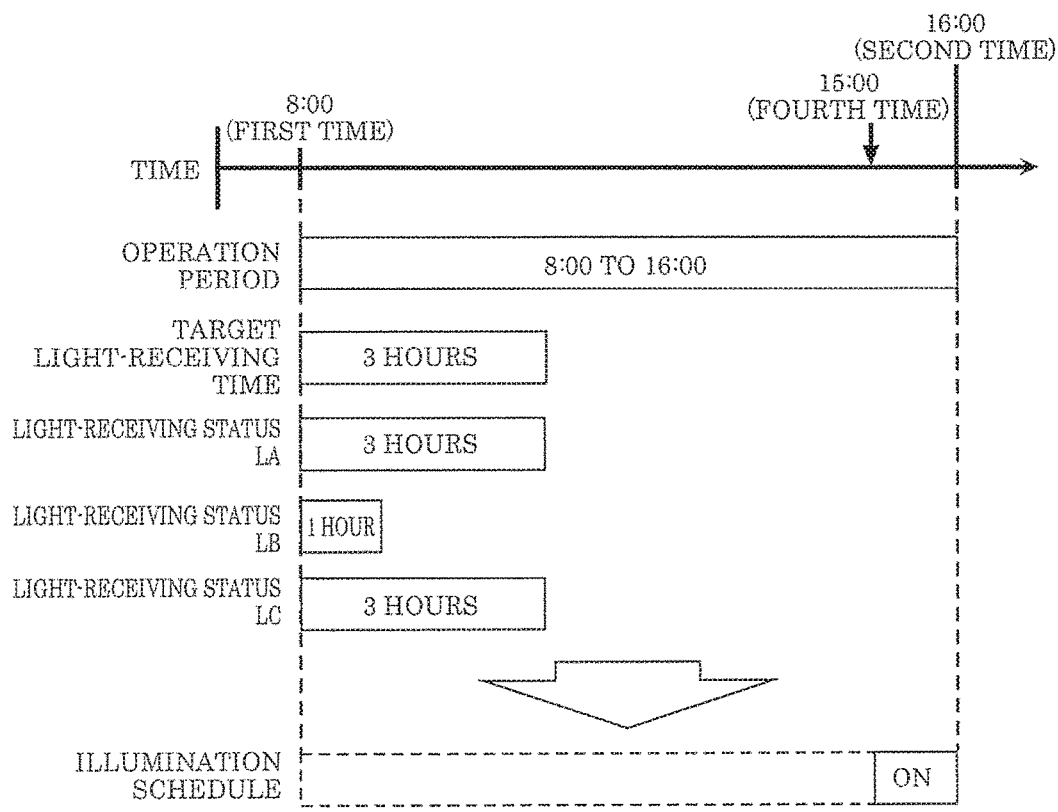
FIG. 8B is a diagram illustrating an illumination schedule that the lighting control system according to the embodiment creates by a fourth time.

FIG. 8B is a diagram illustrating an illumination schedule that lighting control system 100 according to the embodiment creates by the fourth time. It should be noted that FIG. 8B is a diagram indicating an example of Yes in step 502 shown in FIG. 8A.

As shown in FIG. 8B, creating unit 130 determines that subject A and subject C have achieved at least the target light-receiving time because subject A and subject C have a light-receiving time of three hours as indicated by light-receiving status LA of subject A and light-receiving status LC of subject C. In addition, creating unit 130 determines that subject B has not achieved at least the target light-receiving time because subject B has a light-receiving time of one hour as indicated by light-receiving status LB of subject B (Yes in step S502 shown in FIG. 8A). Creating unit 130 updates the illumination schedule for a time period from the fourth time to the second time such that controller 140 causes light source 200 to emit light from the fourth time to the second time.

Referring to FIG. 5 again, after step S208, when, for example, in step S208, lighting control system 100 determines that an underachieving subject who has not achieved at least the target light-receiving time is present among subjects A to C according to the illumination schedule, lighting control system 100 causes light source 200 to emit light from the fourth time to the second time (step S209). Further, lighting control system 100 outputs alert information (step S210). External terminal 600 creates, for example, an image on the basis of the obtained alert information, and notifies subjects A to C.

Figure 8C:
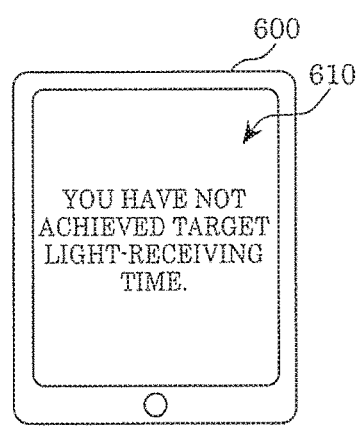
FIG. 8C is a diagram illustrating alert information outputted by the lighting control system according to the embodiment.

FIG. 8C is a diagram illustrating alert information outputted by lighting control system 100 according to the embodiment.

As shown in FIG. 8C, for example, when external terminal 600 obtains the alert information, external terminal 600 causes a display of external terminal 600 to display image 610 such as "You have not achieved target light-receiving time." In this manner, it is possible to urge any of subjects A to C who has not achieved at least the target light-receiving time by the fourth time to receive light from light source 200.

It should be noted that although the alert information is outputted to external terminal 600 operated by subjects A to C, the alert information may be outputted to, for example, notification device 400.

Referring to FIG. 5 again, after step S211 and the second time, subjects A to C output, to lighting control system 100, light-receiving statuses until the second time by operating external terminal 600 (step S212).

Lighting control system 100 determines whether subjects A to C have achieved at least the target light-receiving time, based on the obtained light-receiving statuses of subjects A to C, and outputs a result of the determination to external terminal 600 (step S213).

Figure 9A:
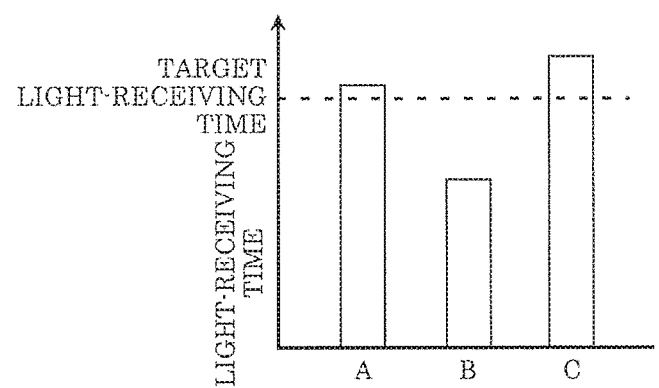
FIG. 9A is a graph for illustrating that the lighting control system according to the embodiment determines an amount of light received by each subject by a second time.

FIG. 9A is a graph for illustrating that lighting control system 100 according to the embodiment determines an amount of light received by each of subjects A to C by the second time. Specifically, FIG. 9A is a graph showing, on the vertical axis, light-receiving times until the second time of subjects A to C.

As shown in FIG. 9A, lighting control system 100 determines whether subjects A to C have receives light for at least the target light-receiving time. For example, in FIG. 9A, lighting control system 100 determines that subject A and subject C have received light for at least the target light-receiving time, and that subject B has not received light for at least the target light-receiving time.

Referring to FIG. 5 again, when external terminal 600 obtains light-receiving time information of subjects A to C from lighting control system 100, external terminal 600 creates an image on the basis of the light-receiving time information, and notifies subjects A to C of whether subjects A to C have received light for at least the target light-receiving time by the second time (step S214).

Figure 9B:
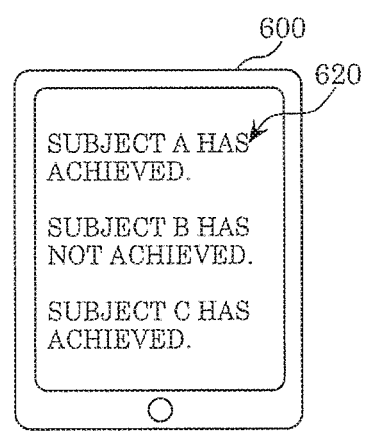
FIG. 9B is a diagram illustrating light-receiving time information indicating light-receiving times until the second time of subjects, which is outputted by the lighting control system according to the embodiment.

FIG. 9B is a diagram illustrating light-receiving time information indicating light-receiving times until the second time of subjects A to C, which is outputted by lighting control system 100 according to the embodiment.

As shown in FIG. 9B, for example, when external terminal 600 obtains the light-receiving time information, external terminal 600 displays image 620 such as "Subject A has achieved," "Subject B has not achieved," and "Subject C has achieved." For example, lighting system 300 is assumed to be installed in a nursing home. In such a case, by checking image 620, a caregiver who cares subjects A to C can urge any of subjects A to C who has not achieved at least the target light-receiving time to receive light for the target light-receiving time the next day.

[Advantageous Effects Etc.]

Lighting control system 100 according to the embodiment is a lighting control system that controls light source 200 that emits light to space R in which subjects stay. Lighting control system 100 includes obtaining unit 110, creating unit 130, and controller 140. Obtaining unit 110 obtains stay schedule information indicating scheduled periods in an operation period after a first time and before a second time later than the first time, the scheduled periods being periods during each of which a corresponding one of the subjects is to stay in space R. Creating unit 130 creates an illumination schedule for causing light source 200 to emit the light, based on the stay schedule information. Controller 140 causes light source 200 to emit the light according to the illumination schedule created. In addition, creating unit 130 creates, based on the stay schedule information, the illumination schedule for (i) allowing the subjects to achieve respective target light-receiving times that are predetermined and for which the subjects receive the light emitted by light source 200, (ii) minimizing a time for which light source 200 emits the light, (iii) causing light source 200 to emit the light during a period including a scheduled period common to at least two of the subject, and (iv) causing light source 200 not to emit the light during a period including a scheduled period common to less than two of the subjects.

With such a configuration, creating unit 130 is capable of creating the illumination schedule for controller 140 to cause light source 200 to emit light during a time period having a large number of the subjects in space R. For this reason, lighting control system 100 is capable of efficiently emitting the light to the subjects by controlling light source 200.

For example, creating unit 130 may create, based on the stay schedule information, the illumination schedule in which periods are included in descending order starting from a period including the highest number of the subjects among the scheduled periods of the subjects.

With such a configuration, creating unit 130 is capable of creating the illumination schedule for controller 140 to cause light source 200 to emit the light during time periods in descending order starting from a time period having the highest number of the subjects in space R. For this reason, lighting control system 100 is capable of efficiently emitting the light to the subjects by controlling light source 200.

Moreover, for example, when at least two periods to be included in the illumination schedule are present, creating unit 130 may create the illumination schedule in which, out of the at least two periods, a period having the earliest time is included.

With such a configuration, creating unit 130 creates the illumination schedule in consideration of an earlier time. For example, it is assumed that some subjects cannot stay in space R as scheduled. Even in such a case, by creating unit 130 creating an illumination schedule in consideration of an earlier time, any subject who was not able to receive light as scheduled is likely to take measures such as receiving light during a time period different from an originally scheduled time period.

Moreover, for example, when obtaining unit 110 obtains instruction information instructing a change of the illumination schedule after the first time, creating unit 130 may recreate an illumination schedule, based on the instruction information.

With such a configuration, for example, there are cases where some subjects cannot stay in space R as scheduled, even in such a case, creating unit 130 is capable of recreating the illumination schedule. As a result, such a configuration allows any subject who was not able to receive light as scheduled to receive light during a time period different from an originally scheduled time period.

Moreover, lighting control system 100 may further include storage 120 that stores the stay schedule information obtained by obtaining unit 110. Creating unit 130 may recreate an illumination schedule at predetermined time intervals, based on the stay schedule information stored in storage 120.

With such a configuration, for example, when lighting control system 100 receives a light-receiving status and stay schedule information of a subject after the first time, lighting control system 100 is capable of automatically recreating the illumination schedule without a user of lighting control system 100 instructing recreation of the illumination schedule. Consequently, such a configuration improves the convenience of lighting control system 100.

Moreover, obtaining unit 110 may obtain the target light-receiving time of each of the subjects. Creating unit 130 may create the illumination schedule for allowing the largest number of the subjects to achieve at least the target light-receiving time, based on the stay schedule information and the target light-receiving time.

With such a configuration, creating unit 130 is capable of creating the illumination schedule for controller 140 to cause light source 200 to emit light during a time period having a large number of the subjects in space R and allowing a larger number of the subjects to receive light for the target light-receiving time. For this reason, lighting control system 100 is capable of more efficiently emitting the light to the subjects by controlling light source 200.

Moreover, creating unit 130 may determine whether the subjects will achieve at least the target light-receiving time, based on the stay schedule information and the target light-receiving time. When creating unit 130 determines that an underachieving subject who will not achieve the target light-receiving time is present among the subjects, controller 140 may output alert information indicating the presence of the underachieving subject.

With such a configuration, lighting control system 100 is capable of notifying any subject who will not receive light for at least the target light-receiving time of information indicating that the subject has not received the light for at least the target light-receiving time, via notification device 400, external terminal 600, etc. Accordingly, the notified subject is likely to take measures such as changing a schedule to receive light.

Moreover, obtaining unit 110 may obtain a light-receiving status after the first time and until a third time before the second time of each of the subjects. Creating unit 130 may determine whether the subjects will achieve at least the target light-receiving time by comparing the light-receiving statuses and the target light-receiving time before the second time. In addition, when creating unit 130 determines that an underachieving subject who will not achieve at least the target light-receiving time is present among the subjects, creating unit 130 may recreate an illumination schedule after the third time.

With such a configuration, for example, there are cases where some subjects cannot stay in space R as scheduled, even in such a case, creating unit 130 is capable of recreating the illumination schedule, based on the reread light-receiving statues of the subjects. For this reason, the subjects can receive light during a time period different from an originally scheduled time period.

Moreover, when creating unit 130 determines that an underachieving subject who will not achieve at least the target light-receiving time is present among the subjects at the third time, controller 140 may output alert information indicating the presence of the underachieving subject.

With such a configuration, lighting control system 100 is capable of notifying any subject who will not receive light for at least the target light-receiving time of information indicating that the subject has not received the light for at least the target light-receiving time, via notification device 400, external terminal 600, etc. Accordingly, the notified subject is likely to take measures such as changing a schedule to receive light.

Moreover, obtaining unit 110 may obtain a light-receiving status after the third time and until a fourth time before the second time of each of the subjects. Creating unit 130 may determine whether the subjects will achieve at least the target light-receiving time by comparing the light-receiving statuses and the target light-receiving time before the second time. When creating unit 130 determines that an underachieving subject who will not achieve at least the target light-receiving time is present among the subjects, controller 140 may output alert information indicating the presence of the underachieving subject, and cause light source 200 to emit the light until the second time.

With such a configuration, lighting control system 100 is capable of notifying any subject who will not receive light for at least the target light-receiving time by the fourth time of information indicating that the subject has not received the light for at least the target light-receiving time, via notification device 400, external terminal 600, etc. In addition, lighting control system 100 causes light source 200 to keep emitting light from the fourth time to the second time. As a result, the subject who received the information indicating that the subject had not received the light for at least the target light-receiving time can go to space R right after receiving the information and can immediately receive light.

Moreover, obtaining unit 110 may obtain a light-receiving status until the second time of each of the subjects. Creating unit 130 may determine whether each of the subjects will achieve at least the target light-receiving time. Controller 140 may output result information indicating a result of the determination by creating unit 130.

For example, lighting system 100 is assumed to be installed in a nursing home. In such a case, by checking image 620, a caregiver who cares subjects can urge any of the subjects who has not achieved at least the target light-receiving time to receive light for the target light-receiving time the next day.

Moreover, lighting system 300 according to the embodiment includes lighting control system 100 and light source 200.

With such a configuration, creating unit 130 is capable of creating the illumination schedule for causing light source 200 to emit light during a time period having a large number of the subjects in space R. For this reason, lighting system 300 is capable of efficiently emitting the light to the subjects.

Moreover, a lighting control method according to the embodiment is a lighting control method executed by a lighting control system that controls light source 200 that emits light to space R in which subjects stay. The lighting control method includes obtaining of stay schedule information, creating of an illumination schedule, and controlling of light source 200. In the obtaining of the stay schedule information, stay schedule information is obtained which indicates scheduled periods in an operation period after a first time and before a second time later than the first time, the scheduled periods being periods during each of which a corresponding one of the subjects is to stay in space R. In the creating of the illumination schedule, an illumination schedule for causing light source 200 to emit the light is created based on the stay schedule information. In the controlling of light source 200, light source 200 is controlled according to the illumination schedule. In addition, in the creating of the illumination schedule, the illumination schedule is created based on the stay schedule information, the illumination schedule being for (i) allowing the subjects to achieve respective target light-receiving times that are predetermined and for which the subjects receive the light emitted by light source 200, (ii) minimizing a time for which light source 200 emits the light, (iii) causing light source 200 to emit the light during a period including a scheduled period common to at least two of the subject, and (iv) causing light source 200 not to emit the light during a period including a scheduled period common to less than two of the subjects.

Such a lighting control method makes it possible to create the illumination schedule for causing light source 200 to emit light during a time period having a large number of the subjects in space R. For this reason, such a lighting control method makes it possible to efficiently emit the light to the subjects.

Moreover, the present disclosure may be implemented as a non-transistor computer-readable recording medium for use in a computer, the recording medium having a computer program recorded thereon for causing the computer to execute the steps included in the lighting control method according to the embodiment.

With this, the computer is capable of executing the lighting control method according to the embodiment can be executed as a program for easily and efficiently emitting light to subjects.

Other Embodiments

Although the lighting control system etc. according to the embodiment has been described above, the present disclosure is not limited to the aforementioned embodiment.

For example, although the creating unit and the controller are implemented through software by a processor executing a program in the aforementioned embodiment, the implementation method is not limited to such, and the creating unit and the controller may be implemented through hardware by using a dedicated electronic circuit including a gate array etc. Moreover, the creating unit and the controller may be implemented as a program including the processes performed by the structural elements in the lighting control system, and as a computer-readable recording medium on which the program is recorded, such as a flexible disk, a hard disk, a CD-ROM, an MO, a DVD, a DVD-ROM, a DVD-RAM, a BD (Blu-ray (registered trademark) Disc), and a semiconductor memory. Further, the program may be distributed via a communication channel such as the Internet.

Specifically, the above-described generic or specific aspects may be implemented by a system, an apparatus, an integrated circuit, a computer program, and a computer-readable recording medium, and may be implemented by any combination of a system, an apparatus, an integrated circuit, a computer program, and a recording medium.

Moreover, for example, although the controller performs switching between on and off of the light source according to the illumination schedule created by the creating unit in the aforementioned embodiment, the present disclosure is not limited to this. The creating unit may create an illumination schedule that specifies an amount of light the light source emits or an illumination schedule that specifies a color of light the light source emits. In addition, when the lighting system includes light sources, the creating unit may specify any of the light sources that is to be turned on/off. The controller may control the dimming/toning of the light source according to the illumination schedule created by the creating unit. In addition, the controller may select a light source that is to be turned on/off, and control the on/off of the light source.

While the foregoing has described one or more embodiments and/or other examples, it is understood that various modifications may be made therein and that the subject matter disclosed herein may be implemented in various forms and examples, and that they may be applied in numerous applications, only some of which have been described herein. It is intended by the following claims to claim any and all modifications and variations that fall within the true scope of the present teachings.

What is claimed is:

1. A lighting control system that controls a light source that emits light to a space in which subjects stay, the lighting control system comprising:
   a communication interface that obtains stay schedule information indicating scheduled periods in an operation period after a first time and before a second time later than the first time, the scheduled periods being periods during each of which a corresponding one of the subjects is to stay in the space; and
   a processor that creates an illumination schedule for causing the light source to emit the light, based on the stay schedule information, and causes the light source to emit the light according to the illumination schedule created,
   wherein the processor creates, based on the stay schedule information, the illumination schedule for (i) allowing the subjects to achieve respective target light-receiving times that are predetermined and for which the subjects receive the light emitted by the light source, (ii) minimizing a time for which the light source emits the light, (iii) causing the light source to emit the light during a period including a scheduled period common to at least two of the subject, and (iv) causing the light source not to emit the light during a period including a scheduled period common to less than two of the subjects,
   the communication interface obtains the target light-receiving time of each of the subjects, and
   the processor creates the illumination schedule for allowing the largest number of the subjects to achieve at least the target light-receiving time, based on the stay schedule information and the target light-receiving time.

2. The lighting control system according to claim 1, wherein the processor creates, based on the stay schedule information, the illumination schedule in which periods are included in descending order starting from a period including a highest number of the subjects among the scheduled periods of the subjects.

3. The lighting control system according to claim 1, wherein when at least two periods to be included in the illumination schedule are present, the processor creates the illumination schedule in which, out of the at least two periods, a period having an earliest time is included.

4. The lighting control system according to claim 1, wherein when the communication interface obtains instruction information instructing a change of the illumination schedule after the first time, the processor recreates an illumination schedule, based on the instruction information.

5. The lighting control system according to claim 1, further comprising:
   a storage that stores the stay schedule information obtained by the communication interface,
   wherein the processor recreates an illumination schedule at predetermined time intervals, based on the stay schedule information stored in the storage.

6. The lighting control system according to claim 1, wherein the processor determines whether the subjects will achieve at least the target light-receiving time, based on the stay schedule information and the target light-receiving time, and
   when the processor determines that an underachieving subject who will not achieve the target light-receiving time is present among the subjects, the processor outputs alert information indicating the presence of the underachieving subject.

7. The lighting control system according to claim 1, wherein the communication interface obtains a light-receiving status after the first time and until a third time before the second time of each of the subjects, and
   the processor determines whether the subjects will achieve at least the target light-receiving time before the second time by comparing the light-receiving statuses and the target light-receiving time, and when the processor determines that an underachieving subject who will not achieve at least the target light-receiving time is present among the subjects, the processor recreates an illumination schedule after the third time.

8. The lighting control system according to claim 7, wherein when the processor determines that an underachieving subject who will not achieve at least the target light-receiving time is present among the subjects at the third time, the processor outputs alert information indicating the presence of the underachieving subject.

9. The lighting control system according to claim 7, wherein the communication interface obtains a light-receiving status after the third time and until a fourth time before the second time of each of the subjects,
   the processor determines whether the subjects will achieve at least the target light-receiving time before the second time by comparing the light-receiving statuses and the target light-receiving time, and
   when the processor determines that an underachieving subject who will not achieve at least the target light-receiving time is present among the subjects, the processor outputs alert information indicating the presence of the underachieving subject, and causes the light source to emit the light until the second time.

10. The lighting control system according to claim 1, wherein the communication interface obtains a light-receiving status until the second time of each of the subjects,
    the processor determines whether each of the subjects will achieve at least the target light-receiving time, and outputs result information indicating a result of the determination by the creating unit.

11. A lighting system, comprising:
the lighting control system according to claim 1; and
the light source.

12. A lighting control method executed by a lighting control system that controls a light source that emits light to a space in which subjects stay, the lighting control method comprising:
  obtaining, by a communication interface, stay schedule information indicating scheduled periods in an operation period after a first time and before a second time later than the first time, the scheduled periods being periods during each of which a corresponding one of the subjects is to stay in the space;
  creating, by a processor, an illumination schedule for causing the light source to emit the light, based on the stay schedule information obtained by the communication interface; and
  controlling, by the processor, the light source according to the illumination schedule created by the processor,
  wherein in the creating, the processor creates, based on the stay schedule information, the illumination schedule for (i) allowing the subjects to achieve respective target light-receiving times that are predetermined and for which the subjects receive the light emitted by the light source, (ii) minimizing a time for which the light source emits the light, (iii) causing the light source to emit the light during a period including a scheduled period common to at least two of the subject, and (iv) causing the light source not to emit the light during a period including a scheduled period common to less than two of the subjects,
  the communication interface obtains the target light-receiving time of each of the subjects, and
  the processor creates the illumination schedule for allowing the largest number of the subjects to achieve at least the target light-receiving time, based on the stay schedule information and the target light-receiving time.

13. A non-transitory computer-readable recording medium for use in a computer, the recording medium having a computer program recorded thereon for causing the computer to execute the lighting control method according to claim 12.

* * * * *